United States Patent
Mori

(10) Patent No.: US 6,344,585 B2
(45) Date of Patent: Feb. 5, 2002

(54) PREPARATION PROCESS OF FLUORENES

(75) Inventor: Hiroaki Mori, Tokyo (JP)

(73) Assignee: Adchemco Corporation, Tokyo (JP)

( * ) Notice: Subject to any disclaimer, the term of this patent is extended or adjusted under 35 U.S.C. 154(b) by 0 days.

(21) Appl. No.: 09/768,621

(22) Filed: Jan. 25, 2001

(30) Foreign Application Priority Data

Jan. 26, 2000 (JP) ......................................... 2000-021861

(51) Int. Cl.[7] .............................................. C07C 59/76
(52) U.S. Cl. ........................ 562/460; 562/403; 562/405; 562/428
(58) Field of Search .................................. 562/403, 405, 562/428, 460; 568/659, 714

(56) References Cited

FOREIGN PATENT DOCUMENTS

EP            1120389        *   8/2001

* cited by examiner

*Primary Examiner*—Paul J. Killos
(74) *Attorney, Agent, or Firm*—Oblon, Spivak, McClelland, Maier & Neustadt, P.C.

(57) ABSTRACT

A tetrahydrofluorene, which is represented by the following formula (I)

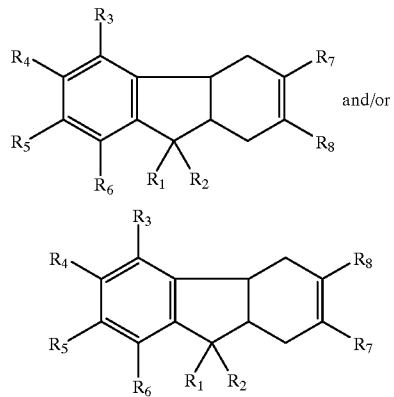

wherein $R_1$ to $R_6$ each independently represent a hydrogen atom or an alkyl group having 1 to 4 carbon atoms, or $R_1$ and $R_2$ are combined together to represent $=O$, $=N$ or $=S$, $R_7$ and $R_8$ each independently represent a hydrogen atom, an alkyl group having 1 to 4 carbon atoms, an alkoxy group having 1 to 4 carbon atoms, a halogen atom, a hydroxyl group or a carboxyl group, is subjected to a hydrogen transfer reaction in the presence of a hydrogen acceptor and a catalyst, whereby a fluorene and a hydride of the hydrogen acceptor are formed at the same time.

10 Claims, No Drawings

PREPARATION PROCESS OF FLUORENES

BACKGROUND OF THE INVENTION a) Field of the Invention

This invention relates to a process for the preparation of raw materials for various resins or intermediates for various chemical products, and more specifically to a process for the industrially advantageous high-yield production of fluorenes as raw materials for epoxy resins, raw materials for function resins such as polycarbonates or polyesters, or raw materials for pharmaceutical products such as anticancer agents from economical raw materials while producing at the same time other compounds useful as various chemical products. It is to be noted that the term "fluorenes" as used herein means fluorene itself and fluorene derivatives having substituent group(s) and position isomers (this definition equally applies to other compounds).

b) Description of the Related Art

Processes heretofore known for the provision of fluorenes include those relying upon their separation and purification from coal tar and those featuring their synthesis. Collection of these compounds, especially as high-purity products, from coal tar is not considered to be an advantageous approach in view of both of technical difficulties and cost, because basically, their contents in coal tar are extremely low.

On the other hand, the known processes for obtaining fluorenes by synthesis include a process involving dehydrocyclization of an alkylbiphenyl compound (U.S. Pat. No. 3,325,551), a process making use of dehydrogenation coupling of a diphenylmethane (PCT/WO 97/17311), and a process relying upon a Pschorr reaction of an o-(1-methylphenyl)aniline [(Ibuki et al., YAKUGAKU ZASSHI, 100(7), 718 (1980))].

Nonetheless, none of the raw material compounds employed in these processes are readily available at low price. Reasons for this problem are postulated to include inter alia: 1) these raw materials themselves are also obtained from coal tar components and hence, require separation and purification; 2) the purified products have to be incorporated in synthesis steps; and 3) the raw material compounds have to be obtained by synthesis. Irrespective of the process, many preparation steps are needed for the provision of a target fluorene. Accordingly, the industrially disadvantageous situation of these synthesis processes cannot be negated.

Incidentally, a process is widely known for the synthesis of a tetrahydrofluorene. According to this process, an indene is subjected as a dienophile together with a butadiene to a Diels-Alder reaction. This synthesis process can readily synthesize fluorenes, each of which contains one or more substituent(s) at particular position(s), by making combined use of dienes and dienophiles having various substituents, respectively, and is considered to be very useful process from the industrial standpoint. Further, dehydrogenation of such tetrahydrofluorenes in the presence of a catalyst can lead to their corresponding fluorenes.

The above-described dehydrogenation can synthesize fluorene with a yield of 90% by reacting tetrahydrofluorene at 250° C. for 5 hours in the presence of a dehydrogenation catalyst such as PD/C. Other tetrahydrofluorenes can also be synthesized into the corresponding fluorenes with yields around 90% under similar reaction conditions. This conventional process, however, requires concentration of a tetrahydrofluorene from a Diels-Alder reaction mixture of the corresponding indene and butadiene by a method such as distillation. Moreover, the dehydrogenation reaction has to be conducted for a time as long as 5 hours or more if one wants to increase the yield of the fluorene. This, however, has developed another problem that the raw materials are partially lost due to polymerization.

SUMMARY OF THE INVENTION

An object of the present invention is, therefore, to provide a process capable of advantageously preparing a fluorene useful as an intermediate for various synthesized organic products and also as a raw material for various resins while preparing another useful compound at the same time.

The above-described object can be achieved by the present invention to be described hereinafter. Namely, the present invention provides a process for the preparation of a fluorene, which comprises subjecting a tetrahydrofluorene, which is represented by the following formula (I)

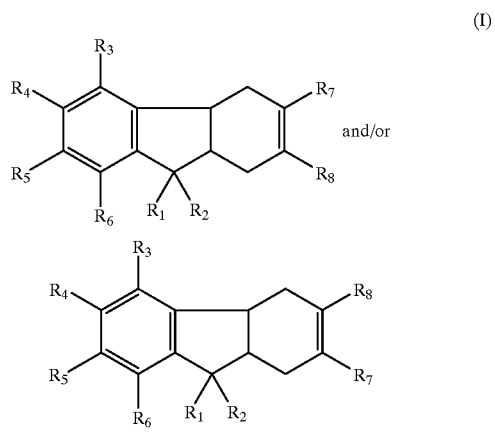

wherein $R_1$ to $R_6$ each independently represent a hydrogen atom or an alkyl group having 1 to 4 carbon atoms, or $R_1$ and $R_2$ are combined together to represent =O, =N or =S, $R_7$ and $R_8$ each independently represent a hydrogen atom, an alkyl group having 1 to 4 carbon atoms, an alkoxy group having 1 to 4 carbon atoms, a halogen atom, a hydroxyl group or a carboxyl group, to a hydrogen transfer reaction in the presence of a hydrogen acceptor and a catalyst, whereby the fluorene and a hydride of the hydrogen acceptor are formed at the same time.

When a fluorene is formed in a hydrogen transfer reaction from a tetrahydrofluorene obtained, for example, by a Diels-Alder reaction, hydrogen is theoretically released from the tetrahydrofluorene. According to the present invention, the hydrogen transfer reaction is conducted in the presence of the hydrogen acceptor. The transfer of hydrogen from the tetrahydrofluorene to the hydrogen acceptor is allowed to proceed almost completely, so that the corresponding fluorene and the corresponding hydride of the hydrogen acceptor are formed with high yields. In addition, the process of the present invention can prepare the fluorene in a shorter time than the conventional dehydrogenation reactions.

DETAILED DESCRIPTION OF THE INVENTION AND PREFERRED EMBODIMENTS

The present invention will next be described more specifically based on preferred embodiments.

The tetrahydrofluorene of the formula (I) for use in the present invention may be collected or synthesized by any process known to date, and no particular limitation is imposed on the tetrahydrofluorene. It is, however, preferred to synthesize it by a Diels-Alder reaction which makes use of an indene of the following formula (I) and a butadiene of the following formula (III):

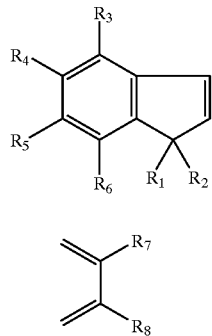

(II)

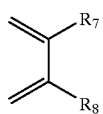

(III)

wherein $R_1$ to $R_8$ have the same meaning as defined above in connection with the formula (I).

In the present invention, it is preferred to obtain the tetrahydrofluorene by the Diels-Alder reaction. Examples of the indene for use in the reaction can include alkylindenes such as indene, methylindene and ethylindene; indanone; and thioindanone. Examples of the butadiene for use in the present invention, on the other hand, can include butadiene, isoprene, 2,3-dimethylbutadiene, chloroprene, 2-hydroxy-1,3-butadiene and 2-methoxy-1,3-butadiene.

The indene and butadiene, which are raw materials, are desirably free of chemical species detrimental to the Diels-Alder reaction, namely, other diene species and dienophiles. The purities of the raw materials are practically immaterial insofar as their impurities do not impair the Diels-Alder reaction. In this case, it is unnecessary to purify the raw materials in advance.

The butadiene for use in the Diels-Alder reaction is used in a smaller amount than the indene in terms of molar ratio. For example, it is preferred to use the butadiene in a proportion of from 0.1 to 0.5 moles per mole of the indene. Use of the butadiene in a proportion lower than the above-described range leads to a problem in that the productivity of the tetrahydrofluorene as the target compound will be unduly low although its yield will be good based on the used butadiene. Use of the butadiene in a proportion beyond the above-described range results in occurrence of many side reactions, leading to a problem in that the yield of the target product will be low based on the used butadiene.

In the Diels-Alder reaction, a catalyst may be added or may not be added. Usable examples of the catalyst can include metal halides such as aluminum chloride, boron trifluoride, titanium chloride, cobalt chloride, vanadium chloride, chromium chloride, manganese chloride, iron chloride, nickel chloride, copper chloride, zinc chloride and tin chloride; metal sulfides; metal sulfates; oxides such as silica and silica alumina; hydrogen halides such as hyrogen chloride and hydrogen bromide; and other acid catalysts. These catalyst may be used preferably in a range of from 0.0002 to 0.2 mole per mole of the butadiene to be used.

The Diels-Alder reaction may preferably be conducted under elevated pressure and an inert gas atmosphere. Usable examples of the inert gas can include nitrogen, helium, carbon dioxide gas and argon, with nitrogen being particularly preferred. The pressure may range from 1 to 100 kg/cm²G, preferably from 5 to 30 kg/cm²G. No particular limitation is imposed on a pressure vessel for use in the present invention, insofar as no catalyst is added to the reaction system. When an acid catalyst is added, the reaction vessel may desirably be made of an anticorrosion material such as "Hastelloy" or otherwise, may desirably be applied with glass lining, "TEFLON" coating or the like.

A solvent may be used provided that it does not take part in the Diels-Alder reaction. It is, however, unnecessary to add a solvent if the reaction raw materials are liquid at the time of the Reaction. The temperature of the Diels-Alder reaction may range from 0 to 250° C., preferably from 120 to 220° C., while the reaction time may range from 1 to 100 hours, preferably from 5 to 20 hours.

In the present invention, the tetrahydrofluorene of the formula (I) can be converted into a fluorene represented by the below-described formula (IV) by subjecting it to the hydrogen transfer reaction in the presence of the hydrogen acceptor and the catalyst. In the reaction, the hydride of the hydrogen acceptor is also obtained at the same time.

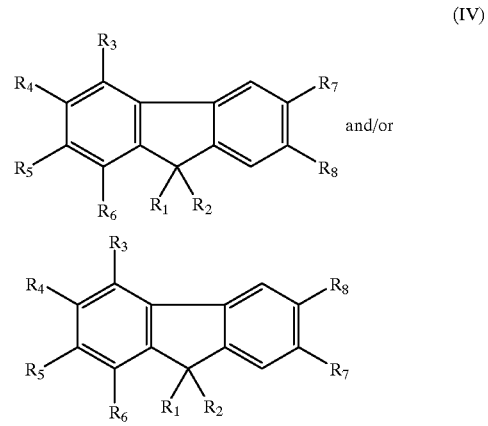

(IV)

wherein $R_1$, to $R_8$ have the same meaning as defined above in connection with the formula (I).

In a first preferred embodiment of the present invention, the tetrahydrofluorene is formed by using the indene in excess of the butadiene (in other words, the butadiene in a smaller amount than the indene) in the above-described Diels-Alder reaction. This can suppress side reactions of the butadiene such as dimerization, thereby making it possible to improve the yield of the tetrahydrofluorene based on the butadiene. On the other hand, use of the unreacted indene, which still remains in the reaction mixture, without its separation as the hydrogen acceptor in the hydrogen transfer reaction of the tetrahydrofluorene in the subsequent step makes it possible to allow the hydrogen transfer reaction of the tetrahydrofluorene to promptly proceed, so that the fluorene is obtained with a high yield in a short time and at the same time, the indane as the hydride of the indene is also obtained with a high yield while minimizing formation of useless byproducts.

A description will next be made about in how much excess of the butadiene the indene should be used in the Diels-Alder reaction. In the case of the hydrogen transfer reaction between the tetrahydrofluorene and the indene, for example, the indene as a hydrogen acceptor is theoretically required in a proportion of 2 moles per mole of the tetrahydrofluorene as a hydrogen donator as will be shown in the following reaction formula (V):

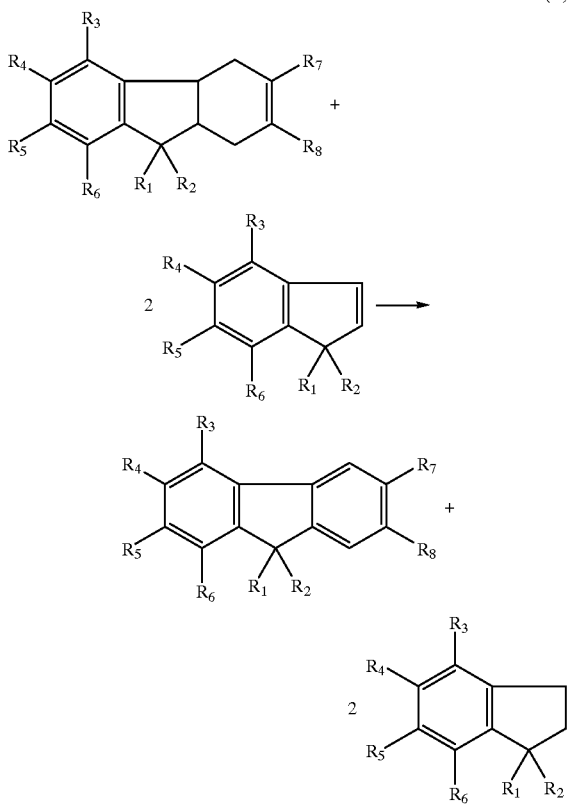

(V)

wherein $R_1$ to $R_8$ have the same meaning as defined above in connection with the formula (I). When primary concern is placed on the production of the fluorene, it is desired to use the indene in excess of the butadiene such that the indene as a hydrogen acceptor remains in a proportion of 2 moles or more per mole of the resulting tetrahydrofluorene in the reaction system. The amounts of the indene and butadiene to be used may be preferably determined such that the indene remains in a proportion of from 2 to 5 moles, notably from 2 to 3 moles per mole of the resulting tetrahydrofluorene.

If the indene exists in the above-described amount in the hydrogen transfer reaction system, the tetrahydrofluorene resulting from the reaction between the indene and the butadiene is quantitatively converted into the fluorene. Accordingly, existence of the indene in a still higher excess does not give any additional influence to the yield of the fluorene but on the contrary, a portion of the indene, said portion taking no part in the hydrogen transfer reaction, is lost through polymerization or the like. Existence of the indene in a proportion higher than 5 moles, preferably 3 moles per mole of the tetrahydrofluorene is not preferred, accordingly. If the indene still remains in a proportion higher than the above-described proportion in the reaction system upon completion of the Diels-Alder reaction, it is preferred to drive off a predetermined amount of the indene from the reaction mixture by distillation and to use the indene distillate again as a raw material in the Diels-Alder reaction.

In a second preferred embodiment of the present invention, the tetrahydrofluorene is formed in a similar manner as in the above-described first embodiment, that is, by using the indene in excess of the butadiene (in other words, the butadiene in a smaller amount than the indene) in the above-described Diels-Alder reaction. This can suppress side reactions of the butadiene, thereby making it possible to improve the yield of the tetrahydrofluorene based on the butadiene. After the unreacted indene in the resultant reaction mixture is distilled off substantially in its entirety, the hydrogen acceptor is added in a proportion of at least 2 moles per mole of the tetrahydrofluorene in the reaction mixture. Hydrogen is then caused to transfer from the tetrahydrofluorene to the hydrogen acceptor, so that the fluorene and the hydride of the hydrogen acceptor are obtained at the same time. As in the first embodiment, this embodiment makes it possible to allow the hydrogen transfer reaction of the tetrahydrofluorene to promptly proceed, so that the fluorene is obtained with a high yield in a short time and at the same time, the hydride of the hydrogen acceptor is also obtained at a high yield while minimizing formation of useless byproducts. The indene, which has been distilled off from the reaction mixture, may preferably be used as a raw material in the Diels-Alder reaction or as a hydrogen acceptor in the hydrogen transfer reaction.

As a modification of the above-described second embodiment, the unreacted indene still remaining in the reaction mixture of the Diels-Alder reaction is distilled off at least partially rather than wholly by distillation. If the amount of the unreacted indene in the reaction mixture is less than 2 moles per mole of the tetrahydrofluorene in the reaction mixture, a hydrogen acceptor is added in an amount such that in the reaction mixture, the hydrogen acceptor and the unreacted indene exist in a total amount of at least 2 moles per mole of the tetrahydrofluorene. Hydrogen is then caused to transfer from the tetrahydrofluorene to the unreacted indene and also to the hydrogen acceptor, whereby a fluorene, an indane and a hydride of the hydrogen acceptor can be formed at the same time. As in the second embodiment, this modification makes it possible to allow the hydrogen transfer reaction of the tetrahydrofluorene to promptly proceed, so that the fluorene is obtained with a high yield in a short time and at the same time, the hydrides of the indene and hydrogen acceptor are also obtained at high yields while minimizing formation of useless byproducts. The indene, which has been distilled off from the reaction mixture, may preferably be used as a raw material in the Diels-Alder reaction or as a hydrogen acceptor in the hydrogen transfer reaction.

The present invention shall not be limited to the above-described first and second embodiments. For example, a tetrahydrofluorene which is available in a manner other than the Diels-Alder reaction may be subjected to a hydrogen transfer reaction in the presence of a hydrogen acceptor and a catalyst such that a fluorene and a hydride of the hydrogen acceptor can be formed at the same time. The hydrogen acceptor may be used in the same proportion as in the second embodiment. The hydrogen acceptor is not limited to an indene, and another hydrogen acceptor may be used. This embodiment can bring about excellent advantageous effects as in the first embodiment. Illustrative of materials usable as the above-described hydrogen acceptor are hydrocarbon compounds containing one or more unsaturated bonds, such as styrenes, dihydronaphthalenes, acenaphthylenes, tetrahydroindenes, benzofurans, indoles and benzothiophenes; and organic compounds containing one or more unsaturated hetero atoms such as —N—, $=$O, and $=$S.

The hydrogen transfer reaction in the process of the present invention is conducted in the presence of a catalyst. A catalyst which has conventionally been employed as a hydrogenation or dehydrogenation catalyst is usable as the catalyst. Examples can include platinum group metal catalysts, transition metal catalysts, metal oxide catalysts, and the like. Illustrative of the platinum group metal catalysts are platinum, palladium, rhodium, ruthenium and indium. Of these, platinum and palladium are preferred. It is particularly preferred to support these precious metals on activated carbon, silica, alumina or the like. Illustrative of the metal catalysts are nickel and copper. It is desired to support these metal catalysts on silica, alumina or the like. Illustrative of the oxide catalysts are zinc oxide, zirconium oxide and vanadium oxide.

The catalyst may be used in an proportion of 0.01 to 10 wt. %, preferably from 0.1 to 5 wt. % (based on the raw materials). The hydrogen transfer reaction may be conducted either in a liquid phase or in a vapor phase. When it is conducted in a liquid phase, the raw materials may be used as are in a solventless manner or may be used after diluting them with a solvent or the like. The reaction temperature may be in a range of from 150 to 350° C., preferably from 200 to 300° C. As a vapor-phase reaction process, the reaction can be conducted in any one of manners of fixed bed, fluidized bed and moving bed. The raw materials may be introduced neat subsequent to vaporization, or may be introduced subsequent to dilution in an inert gas. The SV value of the feed gas may preferably range from 10 to 5,000 $hr^{-1}$, especially from 100 to 1,000 $hr^{-1}$. The reaction temperature may range from 300 to 700° C., with a range of from 350 to 550° C. being particularly preferred.

With the foregoing in view, the tetrahydrofluorene for use in the present invention is prepared, for example, in the following manner when it is used in the Diels-Alder reaction. Predetermined amounts of the indene, butadiene and catalyst, which have been fully dried, are added into an autoclave fitted with an agitator, and the atmosphere in the reaction system is purged. When the raw materials are in the form of gas and liquefied gas (for example, butadiene), the gas and liquefied gas are introduced after the atmosphere in the reaction system has been purged with an inert gas. The Diels-Alder reaction is then conducted at a predetermined reaction temperature for a predetermined time.

From the reaction mixture obtained after completion of the reaction, a predetermined amount of the raw material indene is collected by reduced pressure or atmospheric distillation except for the first embodiment. A concentrate of the tetrahydrofluorene is then collected from the reaction mixture. However, neither the first embodiment nor the second embodiment absolutely requires further collection of the tetrahydrofluorene from the reaction mixture. The tetrahydrofluorene and hydrogen acceptor are then charged into an autoclave fitted with an agitator and a condenser, followed, for example, by the addition of Pd/C (5 wt. % Pd supported on charcoal) in a proportion of around 1 wt. % (based on the reaction mixture). They are then reacted at a temperature of about 250° C. under spontaneous pressure for 2 hours or so, whereby the fluorene and the hydride of the hydrogen acceptor, target compounds, are obtained.

Fluorenes available as described above are useful as intermediates for organic syntheses, and are usable as raw materials for pharmaceutical products, organic functional materials and resins. Further, concurrently-byproduced hydrides of hydrogen acceptors, such as indane, are also useful as raw materials for pharmaceutical products and catalysts.

The present invention will next be described in detail based on Examples and Comparative Examples. It should however be borne in mind that the present invention is by no means limited by the following Examples and Comparative Examples. All designations of "%" in the following Examples and Comparative Examples are on a weight basis unless otherwise specifically indicated.

FIRST EMBODIMENT

Example 1

Crude indene (4 moles) was added into an autoclave fitted with an agitator and a pressure gauge. The atmosphere in the reaction system was purged with nitrogen gas, and the temperature of the crude indene was raised to 200° C. Liquefied indene (1 mole) was then introduced over 2 hours, and the pressure inside the reaction system was adjusted with nitrogen gas to 5 kg/cm$^2$G, followed by a reaction for 6 hours. After completion of the reaction, the reaction mixture was analyzed by gas chromatography. Tetrahydrofluorene was found to have been formed with a yield of 65% (based on butadiene). By reduced pressure distillation of the reaction mixture, excess indene was firstly collected such that the molar ratio of indene to tetrahydrofluorene in the reaction mixture was changed to 2:1, followed by the collection of a 2:1 fraction of indene and tetrahydrofluorene.

A portion of the fraction was charged in an autoclave, and Pd/C (5% Pd supported on charcoal) was added in a proportion of 1% based on the fraction. The resulting mixture was heated to 250° C., followed by a reaction under elevated pressure for 2 hours. After completion of the reaction, the reaction mixture was analyzed by gas chromatography. Fluorene and indane were obtained with a yield of 95% (based on tetrahydrofluorene) and with a yield of 95% (based on indene), respectively.

Example 2

A portion of the 2:1 fraction (by molar ratio) of indene and tetrahydrofluorene obtained in Example 1 was charged in an autoclave, and was then reacted and processed in a similar manner as in Example 1 except that the hydrogen transfer reaction was conducted at 230° C. As a result of an analysis by gas chromatography, fluorene and indane were found to have been formed with a yield of 93% (based on tetrahydrofluorene) and with a yield of 95% (based on indene), respectively.

Example 3

A portion of the 2:1 fraction (by molar ratio) of indene and tetrahydrofluorene obtained in Example 1 was charged in an autoclave, and was then reacted and processed in a similar manner as in Example 1 except that the hydrogen transfer reaction was conducted for 4 hours. As a result of an analysis by gas chromatography, fluorene and indane were found to have been formed with a yield of 98% (based on tetrahydrofluorene) and with a yield of 99% (based on indene), respectively.

Example 4

A portion of the 2:1 fraction (by molar ratio) of indene and tetrahydrofluorene obtained in Example 1 was charged in an autoclave, and was then reacted and processed in a similar manner as in Example 1 except that Pd/C (5% Pd supported on charcoal) was added as a catalyst in a proportion of 3%. As a result of an analysis by gas chromatography, fluorene and indane were found to have been formed with a yield of 96% (based on tetrahydrofluorene) and with a yield of 97% (based on indene), respectively.

Example 5

A portion of the 2:1 fraction (by molar ratio) of indene and tetrahydrofluorene obtained in Example 1 was charged in an autoclave, and was then reacted and processed in a similar manner as in Example 1 except that Pd/C (5% Pd supported on charcoal) was added as a catalyst in a proportion of 0.5%. As a result of an analysis by gas chromatography, fluorene and indane were found to have been formed with a yield of 91% (based on tetrahydrofluorene) and with a yield of 93% (based on indene), respectively.

Example 6

A portion of the 2:1 fraction (by molar ratio) of indene and tetrahydrofluorene obtained in Example 1 was charged in an autoclave, and was then reacted and processed in a similar manner as in Example 1 except that Pd/Al$_2$O$_3$ (5% Pd supported on alumina) was added as a catalyst in a proportion of 1%. As a result of an analysis by gas chromatography, fluorene and indane were found to have been formed with a yield of 96% (based on tetrahydrofluorene) and with a yield of 95% (based on indene), respectively.

Example 7

A 2.5:1 fraction (by molar ratio) of indene and tetrahydrofluorene was collected in a similar manner as in Example 1, followed by a hydrogen transfer reaction in a similar manner as in Example 1. As a result of an analysis by gas chromatography, fluorene and indane were found to have been formed with a yield of 97% (based on tetrahydrofluorene) and with a yield of 88% (based on indene), respectively.

Example 8

Crude indene (4 moles) was added into an autoclave fitted with an agitator and a pressure gauge. The atmosphere in the reaction system was purged with nitrogen gas, and the temperature of the crude indene was raised to 200° C. Isoprene (1 mole) was then introduced over 2 hours, and the pressure inside the reaction system was adjusted with nitrogen gas to 5 kg/cm$^2$G, followed by a reaction for 6 hours. After completion of the reaction, the reaction mixture was analyzed by gas chromatography. Methyltetrahydrofluorene (a mixture of two position isomers) was found to have been formed with a yield of 68% (based on isoprene). By reduced pressure distillation of the reaction mixture, excess indene was firstly collected such that the molar ratio of indene to methyltetrahydrofluorene in the reaction mixture was changed to 2:1, followed by the collection of a 2:1 fraction of indene and methyltetrahydrofluorene.

The fraction was charged in an autoclave, and Pd/C (5% Pd supported on charcoal) was added in a proportion of 1% based on the fraction. The resulting mixture was heated to 250° C., followed by a reaction under spontaneous pressure for 2 hours. After completion of the reaction, the reaction mixture was analyzed by gas chromatography. A mixture of position isomers of methylfluorene was found to have been formed with a yield of 96% (based on methyltetrahydrofluorene), and indane with a yield of 99% (based on indene).

Example 9

Crude indene (4 moles) was added into an autoclave fitted with an agitator and a pressure gauge. The atmosphere in the reaction system was purged with nitrogen gas, and the temperature of the crude indene was raised to 200° C. 2,3-Dimethyl-1,3-butadiene (1 mole) was then introduced over 2 hours, and the pressure inside the reaction system was adjusted with nitrogen gas to 5 kg/cm$^2$G, followed by a reaction for 6 hours. After completion of the reaction, the reaction mixture was analyzed by gas chromatography. Dimethyltetrahydrofluorene was found to have been formed with a yield of 72% (based on 2,3-dimethyl-1,3-butadiene).

By reduced pressure distillation of the reaction mixture, excess indene was firstly collected such that the molar ratio of indene to dimethyltetrahydrofluorene in the reaction mixture was changed to 2:1, followed by the collection of a 2:1 fraction of indene and dimethyltetrahydrofluorene. The fraction was charged in an autoclave, and Pd/C (5% Pd supported on charcoal) was added in a proportion of 1% based on the fraction. The resulting mixture was heated to 250° C., followed by a reaction under spontaneous pressure for 2 hours. After completion of the reaction, the reaction mixture was analyzed by gas chromatography. 2,3-Dimethylfluorene and indane were found to have been formed with a yield of 93% (based on dimethyltetrahydrofluorene) and with a yield of 97% (based on indene), respectively.

Comparative Example 1

Tetrahydrofluorene was synthesized in a similar manner as in Example 1, followed by the collection of a concentrate (purity: 97%) of tetrahydrofluorene from the reaction mixture. The concentrate was then charged in an autoclave, and in a similar manner as in Example 1 except for omission of the hydrogen acceptor, a dehydrogenation reaction was conducted. After completion of the reaction, the reaction mixture was analyzed by gas chromatography. Fluorene was found to have been formed with a yield of 36% (based on tetrahydrofluorene).

Comparative Example 2

A concentrate (purity: 97%) of tetrahydrofluorene, which had been obtained in a similar manner as in Comparative Example 1, was charged in a flask fitted with an agitator and a cooling coil, and Pd/C (5% Pd supported on charcoal) was added in a proportion of 1% based on the concentrate. The resulting mixture was heated to 250° C., followed by dehydrogenation under atmospheric pressure for 6 hours without using any hydrogen acceptor. After completion of the reaction, the reaction mixture was analyzed by gas chromatography. Fluorene was found to have been formed with a yield of 93% (based on tetrahydrofluorene). A long time was, however, needed in this Example to increase the yield.

Comparative Example 3

Dimethyltetrahydrofluorene, which had been synthesized in a similar manner as in Example 9, was collected by distillation from the reaction mixture (purity: 95%), and the concentrate was then charged in an autoclave. Pd/C (5% Pd supported on charcoal) was added in a proportion of 1% based on the concentrate. The resulting mixture was heated to 250° C., followed by dehydrogenation under spontaneous pressure for 2 hours without using any hydrogen acceptor. After completion of the reaction, the reaction mixture was analyzed by gas chromatography. 2,3-Dimethylfluorene was found to have been formed with a yield of 43% (based on dimethyltetrahydrofluorene). The reaction conditions and results in the above-described Examples and Comparative Examples are summarized in Table 1.

As is demonstrated in the above, an indene—which can accept hydrogen released theoretically as a result of formation of a fluorene from a tetrahydrofluorene available from a Diels-Alder reaction—is left over in a reaction system according to the first embodiment of the present invention. As a consequence, the transfer of hydrogen from the tetrahydrofluorene to the indene is allowed to proceed almost completely so that the corresponding fluorene and indane are formed with high yields. Moreover, the process of the first embodiment can prepare the fluorene in a shorter time than the conventional dehydrogenation reactions.

with a yield of 93% (based on tetrahydrofluorene) and with a yield of 90% (based on acenaphthylene), respectively.

Example 2

A hydrogen transfer reaction was conducted in a similar manner as in Example 1 except that benzofuran (2 moles)

TABLE 1

(Reaction conditions and results in examples and comparative examples according to the first embodiment)

| | Raw materials (mol) | | Catalyst | Reaction conditions | | | Yield (%) | |
|---|---|---|---|---|---|---|---|---|
| | THF[1] | Hydrogen acceptor | Amount added (%) | Pressure | Temp. (° C.) | Time (hr) | Fluorene | Indene |
| Ex. 1 | THF (1 mol) | Indene (2 mol) | Pd/C[2] (1 wt. %) | Spontaneous pressure | 250 | 2 | 95 | 95 |
| Ex. 2 | THF (1 mol) | Indene (2 mol) | Pd/C (1 wt. %) | Spontaneous pressure | 230 | 2 | 93 | 95 |
| Ex. 3 | THF (1 mol) | Indene (2 mol) | Pd/C (1 wt. %) | Spontaneous pressure | 250 | 4 | 98 | 99 |
| Ex. 4 | THF (1 mol) | Indene (2 mol) | Pd/C (3 wt. %) | Spontaneous pressure | 250 | 2 | 96 | 97 |
| Ex. 5 | THF (1 mol) | Indene (2 mol) | Pd/C (0.5 wt. %) | Spontaneous pressure | 250 | 2 | 91 | 93 |
| Ex. 6 | THF (1 mol) | Indene (2 mol) | Pd/Al$_2$O$_3$[3] (1 wt. %) | Spontaneous pressure | 250 | 2 | 96 | 95 |
| Ex. 7 | THF (1 mol) | Indene (2.5 mol) | Pd/C (1 wt. %) | Spontaneous pressure | 250 | 2 | 97 | 88 |
| Ex. 8 | MTHF[4] (1 mol) | Indene (2 mol) | Pd/C (1 wt. %) | Spontaneous pressure | 250 | 2 | 96 | 99 |
| Ex. 9 | DMTF[5] (1 mol) | Indene (2 mol) | Pd/C (1 wt. %) | Spontaneous pressure | 250 | 2 | 93 | 97 |
| Comp.Ex. 1 | THF (1 mol) | — | Pd/C (1 wt. %) | Spontaneous pressure | 250 | 2 | 36 | — |
| Comp.Ex. 2 | THF (1 mol) | — | Pd/C (1 wt. %) | Atmospheric pressure | 250 | 6 | 93 | — |
| Comp.Ex. 3 | DMTF (1 mol) | — | Pd/C (1 wt. %) | Spontaneous pressure | 250 | 2 | 43 | — |

[1]THF: tetrahydrofluorene,
[2]5 wt. % Pd supported on charcoal,
[3]5 wt. % Pd supported on alumina
[4]MTHF: methyltetrahydrofluorene,
[5]DMTF: dimethyltetrahydrofluorene

SECOND EMBODIMENT

Example 1

Crude indene (4 moles) was added into an autoclave fitted with an agitator and a pressure gauge. The atmosphere in the reaction system was purged with nitrogen gas, and the temperature of the crude indene was raised to 200° C. Liquefied indene (1 mole) was then introduced over 2 hours, and the pressure inside the reaction system was adjusted with nitrogen gas to 5 kg/cm$^2$G, followed by a reaction for 6 hours. After completion of the reaction, the reaction mixture was analyzed by gas chromatography. Tetrahydrofluorene was found to have been formed with a yield of 65% (based on butadiene). By reduced pressure distillation of the reaction mixture, excess indene was collected, followed by the collection of a fraction of tetrahydrofluorene (purity: 97%).

Into an autoclave, acenaphthylene (2 moles) was charged together with a portion of the tetrahydrofluorene fraction, said portion containing tetrahydrofluorene (1 mole). Pd/C (5% Pd supported on charcoal) was added in a proportion of 1% based on tetrahydrofluorene. The resulting mixture was heated to 250° C., followed by a reaction under spontaneous pressure for 2 hours. After completion of the reaction, the reaction mixture was analyzed by gas chromatography. Fluorene and acenaphthene were found to have been formed was added to the tetrahydrofluorene (1 mole) in a portion of the tetrahydrofluorene fraction obtained in Example 1. After completion of the reaction, the reaction mixture was analyzed by gas chromatography. Fluorene and 2,3-dihydrobenzofuran were found to have been formed with a yield of 95% (based on tetrahydrofluorene) and with a yield of 92% (based on benzofuran), respectively.

Example 3

A hydrogen transfer reaction was conducted in a similar manner as in Example 1 except that indole (2 moles) was added to the tetrahydrofluorene (1 mole) in a portion of the tetrahydrofluorene fraction obtained in Example 1. After completion of the reaction, the reaction mixture was analyzed by gas chromatography. Fluorene and indoline were found to have been formed with a yield of 95% (based on tetrahydrofluorene) and with a yield of 90% (based on indole), respectively.

Example 4

A hydrogen transfer reaction was conducted in a similar manner as in Example 1 except that dihydronaphthalene (2 moles) was added to the tetrahydrofluorene (1 mole) in a portion of the tetrahydrofluorene fraction obtained in Example 1. After completion of the reaction, the reaction mixture was analyzed by gas chromatography. Fluorene and tetralin were found to have been formed with a yield of 95% (based on tetrahydrofluorene) and with a yield of 96% (based on dihydronaphthalene), respectively.

Comparative Example 1

Reference is had to Comparative Example 1 under the First Embodiment.

The reaction conditions and results in the above-described Examples and Comparative Example are summarized in Table 2.

TABLE 2

(Reaction conditions and results in examples and comparative example according to the second embodiment)

| | Raw materials (mol) | | Catalyst | Reaction conditions | | | Yield (%) | |
|---|---|---|---|---|---|---|---|---|
| | THF | Hydrogen acceptor | Amount added (%) | Pressure | Temp. (° C.) | Time (hr) | Fluorene | Hydride |
| Ex. 1 | THF (1 mol) | Acenaphthylene (2 mol) | Pd/C** (1 wt. %) | Spontaneous pressure | 250 | 2 | 93 | 90 |
| Ex. 2 | THF (1 mol) | Benzofuran (2 mol) | Pd/C (1 wt. %) | Spontaneous pressure | 250 | 2 | 95 | 92 |
| Ex. 3 | THF (1 mol) | Indole (2 mol) | Pd/C (1 wt. %) | Spontaneous pressure | 250 | 2 | 95 | 90 |
| Ex. 4 | THF (1 mol) | DHN* (2 mol) | Pd/C (1 wt. %) | Spontaneous pressure | 250 | 2 | 95 | 96 |
| Comp.Ex. 1 | THF (1 mol) | — | Pd/C (1 wt. %) | Spontaneous pressure | 250 | 2 | 36 | — |

*DHN: dihydronaphthalene,
**5 wt. % Pd supported on charcoal

As is demonstrated in the above, a hydrogen acceptor—which can accept hydrogen released theoretically as a result of formation of a fluorene from a tetrahydrofluorene available from a Diels-Alder reaction—is added to the a reaction system according to the second embodiment of the present invention. As a consequence, the transfer of hydrogen from the tetrahydrofluorene to the hydrogen acceptor is allowed to proceed almost completely so that the corresponding fluorene and the corresponding hydride of the hydrogen acceptor are obtained with high yields. Moreover, the process of the second embodiment can prepare the fluorene in a shorter time than the conventional dehydrogenation reactions.

What is claimed is:

1. A process for the preparation of a fluorene, which comprises subjecting a tetrahydrofluorene, which is represented by the following formula (I)

(I)

and/or

-continued wherein $R_1$ to $R_6$ each independently represent a hydrogen atom or an alkyl group having 1 to 4 carbon atoms, or $R_1$ and $R_2$ are combined together to represent =O, =N or =S, $R_7$ and $R_8$ each independently represent a hydrogen atom, an alkyl group having 1 to 4 carbon atoms, an alkoxy group having 1 to 4 carbon atoms, a halogen atom, a hydroxyl group or a carboxyl group, to a hydrogen transfer reaction in the presence of a hydrogen acceptor and a catalyst, whereby said fluorene and a hydride of said hydrogen acceptor are formed at the same time.

2. A process according to claim 1, wherein said hydrogen acceptor is selected from the group consisting of unsaturated compounds and mixtures thereof.

3. A process according to claim 2, wherein said unsaturated compounds consist of indenes, dihydronaphthalenes, benzofurans and indoles.

4. A process according to claim 1, wherein said tetrahydrofluorene is a tetrahydrofluorene contained in a reaction mixture available from a Diels-Alder reaction between an indene, which is represented by the following formula (II):

(II)

wherein R₁ to R₆ have the same meaning as defined above in connection with the formula (I), and a butadiene represented by the following formula (III):

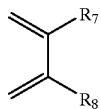

(III)

wherein R₇ and R₈ have the same meaning as defined above in connection with the formula (I).

5. A process according to claim 4, which comprises:

reacting said indene and said butadiene in a state that said indene exists in excess in terms of molar ratio, thereby obtaining a reaction mixture with said tetrahydrofluorene contained therein;

adjusting the amount of an unreacted portion of said indene in the resultant reaction mixture to at least 2 moles per mole of said tetrahydrofluorene in said reaction mixture; and transferring hydrogen from said tetrahydrofluorene to said indene while using said indene as a hydrogen acceptor, whereby a fluorene and an indane are formed at the same time.

6. A process according to claim 4, which comprises:

reacting said indene and said butadiene in a state that said indene exists in excess in terms of molar ratio, thereby obtaining a reaction mixture with said tetrahydrofluorene contained therein;

distilling off an unreacted portion of said indene from the resultant reaction mixture;

adding at least 2 moles of a hydrogen acceptor per mole of said tetrahydrofluorene in said reaction mixture; and transferring hydrogen from said tetrahydrofluorene to said hydrogen acceptor, whereby a fluorene and a hydride of said hydrogen acceptor are formed at the same time.

7. A process according to claim 4, which comprises:

reacting said indene and said butadiene in a state that said indene exists in excess in terms of molar ratio, thereby obtaining a reaction mixture with said tetrahydrofluorene contained therein;

if the amount of an unreacted portion of said indene in the resultant reaction mixture is less than 2 moles per mole of said tetrahydrofluorene in said reaction mixture, adding a hydrogen acceptor in an amount such that said hydrogen acceptor and said unreacted portion of said indene exist in a total amount of at least 2 moles per mole of said tetrahydrofluorene; and transferring hydrogen from said tetrahydrofluorene to said unreacted portion of said indene and also to said hydrogen acceptor, whereby a fluorene, an indane and a hydride of said hydrogen acceptor are formed at the same time.

8. A process according to any one of claims 4 to 7, wherein said indene is at least one indene selected from the group consisting of indene, methylindene, ethylindene, indanone and thioindanone.

9. A process according to any one of claims 4 to 7, wherein said butadiene is at least one butadiene selected from the group consisting of butadiene, isoprene, 2,3-dimethylbutadiene, chloroprene, 2-hydroxy-1,3-butadiene and 2-methoxy-1,3-butadiene.

10. A process according to anyone of claims 4 to 7, wherein said butadiene is used in a proportion of from 0.1 to 0.5 mole per mole of said indene.

* * * * *